(12) United States Patent
Woodall

(10) Patent No.: US 8,647,375 B2
(45) Date of Patent: Feb. 11, 2014

(54) MULTI-FUNCTION BEDSIDE CARE AND THERAPY SYSTEM

(75) Inventor: Charlene Woodall, Weiser, ID (US)

(73) Assignee: Charles Woodall

( * ) Notice: Subject to any disclaimer, the term of this patent is extended or adjusted under 35 U.S.C. 154(b) by 367 days.

(21) Appl. No.: 12/902,743

(22) Filed: Oct. 12, 2010

(65) Prior Publication Data

US 2012/0089210 A1    Apr. 12, 2012

(51) Int. Cl.
*A61F 7/00* (2006.01)
*A61H 33/00* (2006.01)

(52) U.S. Cl.
USPC .................................. 607/104; 607/82; 4/597

(58) Field of Classification Search
USPC .......... 607/96, 104, 108–111, 82; 4/596–614; 312/209; D34/5, 12–27; 601/154, 601/159–161
See application file for complete search history.

(56) References Cited

U.S. PATENT DOCUMENTS

| | | | | |
|---|---|---|---|---|
| 3,867,939 A | * | 2/1975 | Moore et al. | 604/291 |
| 4,523,594 A | * | 6/1985 | Kuznetz | 607/104 |
| 7,000,682 B2 | * | 2/2006 | Chambers | 165/46 |
| 7,819,835 B2 | * | 10/2010 | Landy et al. | 604/6.13 |
| 2002/0091431 A1 | * | 7/2002 | Gunn et al. | 607/110 |
| 2006/0287697 A1 | * | 12/2006 | Lennox | 607/96 |

* cited by examiner

*Primary Examiner* — Linda Dvorak
*Assistant Examiner* — Adam Avigan
(74) *Attorney, Agent, or Firm* — Don Meeker, Patent Agent

(57) ABSTRACT

A wheeled cart has liquid cooling and liquid heating devices separated by thermal insulation. Pumps circulate cooled liquid and heated liquid through hoses to cooled packs and heated packs of patient treatment. Thermostats control the temperature and continual re-circulation of the cooled and heated liquids through the packs to maintain the proper temperature at all times without changing the packs.

11 Claims, 2 Drawing Sheets

MULTI-FUNCTION BEDSIDE CARE AND THERAPY SYSTEM

CROSS-REFERENCE TO RELATED APPLICATIONS

Not Applicable.

STATEMENT REGARDING FEDERALLY SPONSORED RESEARCH OR DEVELOPMENT

Not Applicable.

THE NAMES OF THE PARTIES TO A JOINT RESEARCH OR DEVELOPMENT

Not Applicable.

BACKGROUND OF THE INVENTION

1. Field of the Invention

The present invention relates to patient care and particularly to a multi-function bedside care and therapy system comprising a wheeled cart with water cooling (ice machine) and water heating devices in the cart with separate water pumps circulating water to a cold water pack and a hot water pack with cold and hot water, respectively, continually re-circulating through the packs to maintain the proper temperature at all times without changing the packs; the cart further comprises a hose and shower head for washing patients, shelves for towels and other patient care supplies, retractable power cords and a back-up battery.

2. Description of Related Art Including Information Disclosed Under 37 CFR 1.97 and 1.98

Topical application of heat or cold, respectively, to selected regions of the body is used to treat a wide variety of medical/surgical conditions in hospitals, nursing homes, and other care giving locations such as home health care and sports medicine clinics. One difficulty with conventional hot and cold packs applied to bodies of patients is that the packs change temperature rapidly and need continual replacement. The prior art does not adequately solve this problem.

A number of prior art inventors have devised cold therapy systems wherein cold water is continuously circulated through a pad by means of a pump. Examples of such a system are taught in U.S. Pat. Nos. 5,241,951 and 5,330,519. Both employ a cooler with ice to cool the water.

More devices for circulating a cooling and/or heating fluid through a blanket or pad applied to a patient have also been proposed for regulating the patient's temperature. Examples of such devices are shown in U.S. Pat. Nos. 2,726,658; 2,885,189; 3,007,473; 3,894,213; 3,587,577; 3,918,458; 3,967,627; 4,026,299; 4,459,468; 4,523,594; 4,962,761; 4,691,762; 4,884,304; 5,097,829; 5,170,783; 5,324,318; 5,330,361; 5,431,622; 5,486,207; 5,865,841; 5,871,526; 6,197,045; 6,375,674 and 6,692,518. However those devices are not portably contained within or sitting upon a wheeled cart and do not provide an ice maker.

U.S. Pat. No. 1,896,953, issued Feb. 7, 1933 to Hassell, describes a wheeled cart with an electric ice pack. The device has a flexible pad having internal passages through which is circulated a cold or warm fluid by means of a pump. The pump assembly includes a reservoir for the liquid, a compressor and cooling element, a heater to warm the liquid when desired and means for selecting a desired temperature and maintaining the liquid at that temperature.

U.S. Pat. No. 5,591,220, issued Jan. 7, 1997 to Mahawili, provides a fluid replacement apparatus for use with a portable body heating and cooling system which is provided with a body or frame that may be supported by caster wheels, for example, for facile transportation of the apparatus. The apparatus includes a frame with a support portion configured for supporting a reservoir of the portable body heating and cooling system. A heat exchange mechanism is retained in the frame. The heat exchange mechanism includes a thermostatically controlled receptacle for maintaining fluid circulating through the receptacle at a desired temperature. A cover member covers the reservoir to releasably couple the fluid replacement apparatus to the portable body heating and cooling system. The cover member includes a pump for circulating fluid between the heat exchange mechanism and the reservoir of the portable body heating and cooling system. Return and supply tubes extend between the cover member and the heat exchange mechanism. The supply tube is coupled to the pump and to a receptacle of the heat exchange mechanism for circulating fluid from the reservoir to the receptacle. The return tube is coupled to the receptacle and extends through the cover member for circulating fluid from the receptacle to the reservoir at the desired temperature, for maintaining the temperature of the fluid in the reservoir at the desired temperature.

Two U.S. Patents, U.S. Pat. No. 7,001,417 issued Feb. 21, 2006 and U.S. Pat. No. 6,551,347 issued Apr. 22, 2003 to Elkins, concern a cooling/heating system for thermal therapy of patients. The equipment includes a flexible heat exchange structure having fluid conducting channels formed between two layers of flexible material, with improved liquid manifolds at the ends of the channels for resisting pinching, crimping or buckling in the manifolds on pressurization and when the heat exchange structure is subjected to flexure as when worn on the human body. The manifolds are configured so that pressurization shrinkage at the manifold is balanced with pressurization shrinkage laterally among the fluid conducting channels. In a preferred embodiment, the fluid conducting channels themselves are configured in a zigzag pattern which is effective to resist buckling or pinching of the channels when the heat exchange structure is subjected to bending. In a further embodiment the flexible heat exchange structure includes a third layer of material to form a pressurized air envelope, for heat/cold and pressure thereby. The heat exchange structure can be in combination with a cooperating portable device, which may be in the form of a wheeled cart, for providing heating and/or cooling liquid to the patient therapy device at a desired temperature, with or without cyclic pressurization.

U.S. Pat. No. 6,551,348, issued Apr. 22, 2003 to Blalock et al, is for a temperature controlled therapy device which maintains a desired temperature in a fluid. The temperature controlled therapy device includes a fluid reservoir, a temperature controlled fluid, a watertight blanket having an internal space located therewith, a conduit connected between an exit port of the reservoir and an entry port of the blanket and between an exit port of the blanket and an entry port of the reservoir for defining a fluid circuit within which the temperature controlled fluid may circulate, a pump for circulating the temperature controlled fluid through the fluid circuit, a differential temperature sensor for generating an output signal proportional to a difference in fluid temperature in the blanket and a temperature at a remote location, an absolute temperature sensor for generating an output signal proportional to the temperature at the remote location, a control circuit having as inputs the outputs of the differential temperature sensor and the absolute temperature sensor for generating a control signal for operating the pump in order to maintain a defined temperature range in the fluid in the blanket, and a power supply for supplying power to the device.

U.S. Pat. No. 4,662,433, issued May 5, 1987 to Cahn et al, discloses a blanket which allows personal heat control, particularly cooling. More specifically, the blanket is provided with internal ducts through which a stable foam is circulated as a cooling fluid in such a way that the inside of the blanket facing the person being cooled is maintained at a temperature slightly below body temperature, while the outside of the blanket is insulated to minimize heat exchange with the environment. Compared to the use of a liquid as the circulating cooling fluid, foam is very light and thus minimizes the weight of the blanket, but it has better heat transfer properties and heat capacity than a gas. Cooling of the recirculating cooling fluid is done separate from the blanket in a refrigeration unit connected to the blanket by a feed and return duct. The refrigeration unit can operate by means of a heat pump, or use a stored refrigerant such as ice, or employ a continuous coolant, such as tap water.

U.S. Pat. No. 5,336,249, issued Aug. 9, 1994 to Mahawili, shows a portable body heating/cooling system and method of use for thermal treatment of selected body portions such as joints, muscles and the like, a reservoir being insulated for containing hot fluid or ice water, an elongated and flexible thermal pad having one surface formed by conductive and flexible tubular conduits for conforming to the selected body portion and for producing thermal treatment by the flow of fluid through the tubular conduits, the tubular conduits being connected with the reservoir by non-collapsible supply and return tubes, and a pump preferably battery operated and preferably located in the reservoir for continually circulating fluid from the reservoir through the tubular conduits and back to the reservoir, the thermal pad being equipped with a retainer for securing the thermal pad in contact with the selected body portion, the supply and return tubes preferably being accordion-like in configuration to assure constant circulation of fluid through the thermal pad, the conduit also preferably being corrugated.

U.S. Pat. No. 4,844,072, issued Jul. 4, 1989 to French et al, claims a system for circulating hot or cold liquid through a pad placed in thermal contact with a patient for thermal therapy. The system includes a flexible thermal pad with an internal channel for carrying the liquid and a pump assembly for circulating and optionally heating the liquid. The patient-contacting surface of the pad comprises a foam having a cushioned surface to reduce the risk of ischemia and enhance patient comfort. An open-cell foam structure absorbs and retains moisture for applying moist heat. The system is microprocessor controlled and includes a heater to warm the liquid to a selectable temperature for heat therapy. A display selectively indicates set-point or actual liquid temperature in either .degree. F. or .degree. C. as desired. Safety features include three separate over-temperature sensors, a tilt switch and a float switch which de-energize both the heater and the pump when an abnormal temperature is sensed, the unit is tipped or a low liquid level is sensed, respectively. A sealed membrane switch assembly protects the unit from spills and includes a concealed set-point switch to prevent unauthorized tampering. Set-point may be decremented to a "heater off" position to permit the circulation of unheated liquid. The temperature controller automatically recalibrates itself periodically.

U.S. patent application #20050279847, published Dec. 22, 2005 by Kim, indicates a hot water circulating pump having a water heating unit, and a hot water mat using the same. The hot water circulating pump is disposed outside of the water heating unit to prevent each part of the circulating pump from being damaged due to water leakage into the circulating pump. The hot water mat is improved in structure to allow the hot water tube to be disposed within the hot water mat, thereby providing simplicity and convenience in assembly.

U.S. patent application #20080125839, published May 29, 2008 by Kelner et al, concerns a thermal pump for controlling air bubbles, thermal therapy to allow the patient to perceive that the thermal therapy is constantly being applied, and ensure the appropriate amount of water flows through the thermal pump. The patient application device can be a cushion, a blanket, a wrap-around unit, a tub, drip applicator, and/or body core adjusting device.

Three U.S. patent applications, #20080269852 published Oct. 30, 2008; #20060287697 published Dec. 21, 2006 and #20060030915 published Feb. 9, 2006 by Lennox et al, put forth a body thermal regulation system which includes a thermal exchange collar for application to a neck of a patient, a thermal regulation pad for application to a body region, such as an axilla region of the patient, and a thermal regulation cap for application to a head of the patient. The pump console is situated on a wheeled cart for portability. Each device uses ice for cooling the patient.

U.S. Pat. No. 7,056,334, published Jun. 6, 2006 by Lennox, illustrates a thermal delivery system includes a base unit having a thermal regulation source and a console configured to deliver cooling fluid to a body-cooling device to induce hypothermia and aid in resuscitation of a patient. When a user docks the console with the base station, the console thermally contacts the thermal regulation source. The thermal regulation source alters the temperature of fluid held by the console for an indefinite period of time. In the case where a patient, at a location remote from the thermal delivery system, requires induction of hypothermia, a user detaches the console from the base station and transports the console to the patient's location. The configuration of the thermal delivery system allows the base station to thermally adjust the temperature of the fluid held by the console for an extended period of time, thereby minimizing a delay in transporting a console having the thermally adjusted fluid to the patient.

U.S. Pat. No. 6,962,600, issued Nov. 8, 2005 to Lennox et al, indicates a cooling system includes a pressurized liquid refrigerant source having a liquid refrigerant and a cooling garment coupled to the liquid refrigerant source, which may be contained within a crash cart. The cooling garment defines chambers containing a heat transfer fluid. During operation, a user places the cooling garment in thermal communication with a body portion of a subject. As the cooling garment receives the liquid refrigerant from the pressurized source, the liquid refrigerant thermally contacts the heat transfer fluid and evaporates, thereby reducing the temperature of the heat transfer fluid. The heat transfer fluid, in turn, reduces the temperature of the body portion in thermal communication with the cooling garment. The heat transfer fluid acts to substantially evenly distribute cooling, as provided by the evaporation of the liquid refrigerant, to the body portion contacting the cooling garment to minimize localized "cold spots" within the chamber.

U.S. Pat. No. 7,008,445, issued Mar. 7, 2006 to Lennox, puts forth a system and method for inducing therapeutic levels of hypothermia in a patient in the urgent care setting. The system consists of a small battery operated console and one or more garments. The garments are connected to the console by one or more umbilicals. The console provides cold fluid to the garments under pressure and the garment cools the surface of the body. Fluid returns from the garment back to the console in a closed loop fashion. The console contains an electrical battery and a thermal battery that provides operation of the system for more than one hour. The body cooling system disclosed above may be configured where a thermal battery, as a separate component is not required for operation, instead, ice may be placed into the reservoir, where the ice in the reservoir provides body cooling.

U.S. Pat. No. 7,547,320, issued Jun. 16, 2009 to Schook et al, illustrates an apparatus for altering the body temperature of a patient. A method of performing CPR on the patient while altering the body temperature of a patient is provided which comprises covering at least a thoracic region of the patient with a cover. A heat transfer liquid is directed to flow through liquid passages in the cover for contact with the thoracic region of the patient. Oxygen is supplied to the lungs of the patient, and the thoracic region of the patient is compressed directly through the cover while heat transfer liquid is being directed through the liquid passages in the cover. Apparatus for adjusting the body temperature of a patient generally comprising an enclosure sized and shaped for receiving at least a torso of the patient's body. A heat transfer liquid has a temperature between about 0.degree. C. and about 5.degree. C. A pump drives the heat transfer liquid into the enclosure for connect with the patient's body at a rate greater than about 6 liters per minute. A mobile cart houses the control system.

What is needed is a multi-function bedside care and therapy system comprising a wheeled cart with water cooling (ice machine) and water heating devices in the cart with separate water pumps circulating water to a cold water pack and a hot water pack with cold and hot water, respectively, continually re-circulating through the packs to maintain the proper temperature at all times without changing the packs.

BRIEF SUMMARY OF THE INVENTION

An object of the present invention is a multi-function bedside care and therapy system comprising a wheeled cart with water cooling (ice machine) and water heating devices in the cart with separate water pumps circulating water to a cold water pack and a hot water pack with cold and hot water, respectively, continually re-circulating through the packs to maintain the proper temperature at all times without changing the packs.

In brief, the present invention is encased in a compact stainless steel cabinet that rolls up to the client. Inside are tanks that hold water. A small plastic water pump, a small instant water heater, and the proper tubing to take the water through the tubing up to the inflatable body pads. An electric plug in (adapter) with time release controls a small ice maker to keep the cold pack water cold.

Filled with cold tap water, and ice on top, the ice water is pumped through the rubber tubing that is approximately 5 ft long ½ inch wide that travels up to a soft plastic waterproof pad that can be made in various sizes. The tubing becomes smaller, as it travels closer to the pad. Small tubes inside the pad circulate the water around in the pad. Another ½ inch rubber tube of 5 ft long sits along the side of the other rubber tube in which it delivers the water from the inflated pad, and it drains back down into the cold water. Ice is needed to sit on top of the water to keep the water cold. Without ice however, the warmth of the body warms the water too quickly. This procedure makes excellent ice packs. Hot packs can be used in the same manner with controlled time released heat, created from an instamatic water heater. With the internal plumbing cleansing, and bathing are another excellent function.

The present invention would be used in hospitals, nursing care facilities, physical therapy facilities, doctors offices, at home, or anywhere a hot pack or a cold pack is needed.

The cold packs are generally used to reduce a fever, reduce edema in different parts of the body, and reduce pain, and swelling from post surgery clients.

The hot packs are generally used to increase circulation, to help in healing infections, bring relief to sore muscles, and arthritis.

The multi-function cart may also be used in bathing-cleansing a patient.

The present invention would be a time and money saver. The present invention would eliminate running to a freezer for expensive pre-made ice packs that drip and don't last long. The present invention would also eliminate heating hot packs in the microwave which has caused lawsuits from infections on clients in the hospitals from burns caused from hot overheated packs. Wound cleansing and dry or wet baths can be given with ease to incapacitated clients. With the battery backup the present invention can be used even if the electricity fails.

BRIEF DESCRIPTION OF THE SEVERAL VIEWS OF THE DRAWINGS

These and other details of my invention will be described in connection with the accompanying drawings, which are furnished only by way of illustration and not in limitation of the invention, and in which drawings.

DETAILED DESCRIPTION OF THE INVENTION

Figure 1:
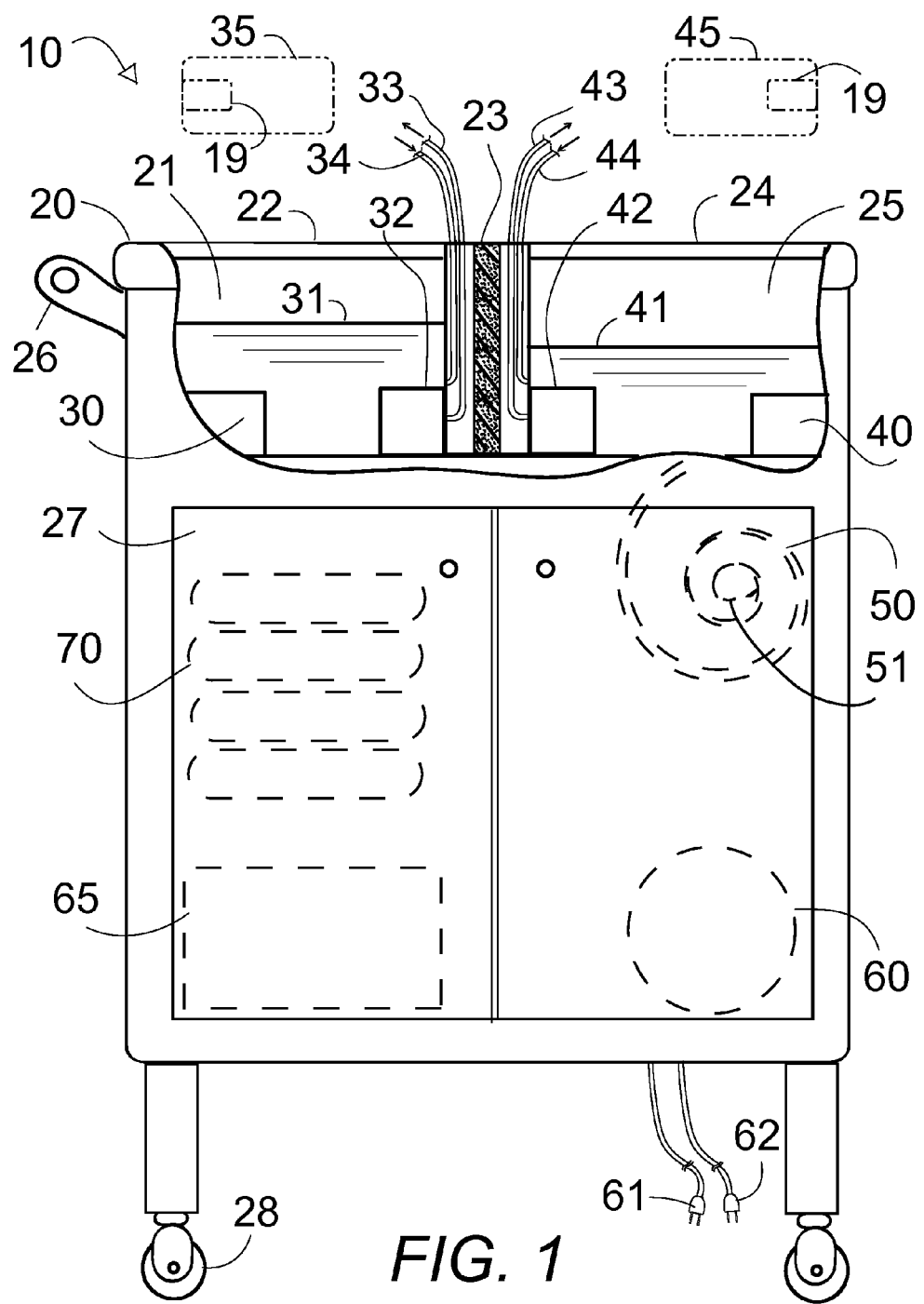
FIG. 1 is a front elevational view of the multi-function bedside care and therapy wheeled cart of the present invention.
Figure 2:
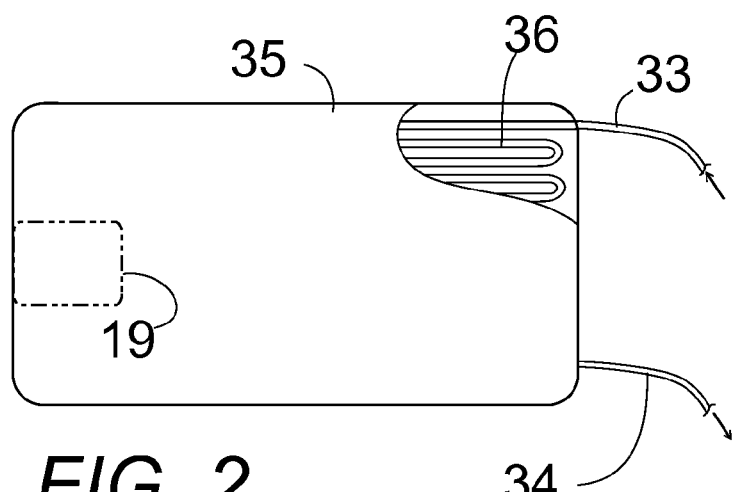
FIG. 2 is a plan view of a cold pack used with the multi-function bedside care and therapy wheeled cart of the present invention with constant circulation of cold water at a controlled temperature through the cold pack.
Figure 3:
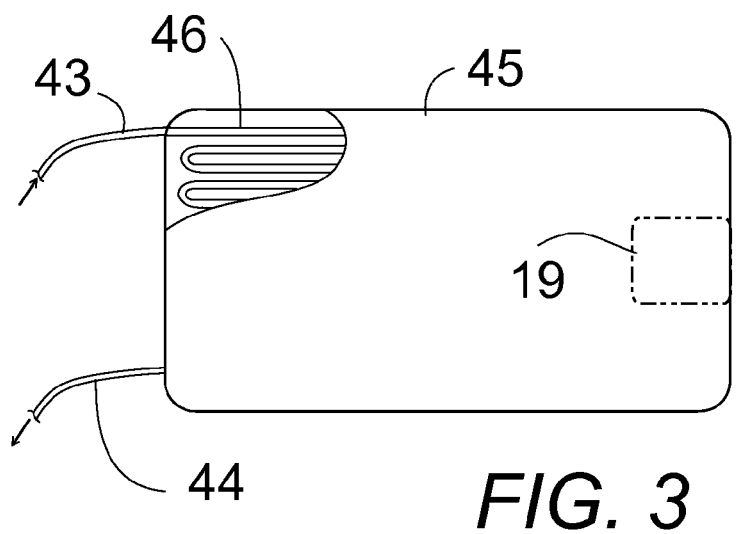
FIG. 3 is a plan view of a heat pack used with the multi-function bedside care and therapy wheeled cart of the present invention with constant circulation of heated water at a controlled temperature through the heat pack.

In FIGS. 1-3, a multifunction bedside care and therapy apparatus 10 comprising a wheeled cart 20 for bedside use with a temperature controlled cooled liquid 31 circulated through a cooled liquid pack 35 placed on a patient and a separate temperature controlled heated liquid 41 circulated through a heated liquid pack 45 placed on a patient; thereby providing a multi-function bedside care and therapy system having a cooled liquid pack and heated liquid pack with cooled and heated liquid, respectively, continually circulating through them to maintain the proper temperature at all times without changing the packs.

The wheeled cart 20 comprises a means 30 for cooling a liquid, which is preferably an ice cube maker communicating with the liquid 31 in the tank 21, to create a temperature controlled cooled liquid 31 in the tank 21 with a cover 22. In FIGS. 1 and 2, a cooled liquid pack 35 with a serpentine circulating internal cooling liquid tube 36 is applied to a patient. A means 32 for re-circulating the cooled liquid 31 through the cooled liquid pack 35 preferably comprises cooling liquid pump 32 in the cooling liquid tank 21. A thermostat 19 on the cooled liquid pack 35 or located elsewhere in the system preferably serves as a means for monitoring the temperature of the cooled liquid and for controlling the means 30 for cooling the liquid to maintain the cooled liquid at a desired temperature.

The cooled liquid pump 32 communicates with the tank 21 for holding the temperature controlled cooled liquid and a cooled liquid input hose 33 transporting the temperature controlled cooled liquid from the cooled liquid pump to the cooled liquid pack 35 on the patient and a return cooled liquid hose 34 transporting the cooled liquid from the cooled liquid pack back into the tank 21 for holding the temperature controlled cooled liquid.

A separate means 40 for heating a liquid, preferably a liquid heater, creates a temperature controlled heated liquid 41 in a tank 25 for holding the temperature controlled heated liquid. In FIGS. 1 and 3, a heated liquid pack 45 with a serpentine circulating internal cooling liquid tube 46 is applied to a patient. A means 40 for re-circulating the heated liquid through the heated liquid pack 45 preferably comprises a heated liquid pump. A thermostat 19 on the heated liquid pack 45 serves as the means for monitoring the temperature of the heated liquid and for controlling the means 40 for heating the liquid to maintain the heated liquid at a desired temperature.

A first interior space, a cooled water tank 21, within the wheeled cart 20 houses the means 30 for cooling the liquid 30 and temperature controlled cooled liquid 31. A second interior space, a heated liquid tank 25 within the wheeled cart 20 houses the means 40 for heating the liquid and the temperature controlled heated liquid 41. The first and second interior tank spaces 21 and 25 are separated by an insulation means 23 for thermally insulating the two interior tank spaces 21 and 25 from each other.

The heated liquid pump 40 communicates with the liquid 41 in the second tank 25 and a heated liquid input hose 43 transporting the temperature controlled heated liquid 41 from the heated liquid pump 40 to the heated liquid pack 45 on the patient and a heated liquid return hose 44 transports the heated liquid from the heated liquid pack back 45 into the second tank 25 for holding the temperature controlled heated liquid.

The apparatus preferably further comprises a coiled hose 50 and a shower head 51 housed within the wheeled cart 20 for washing patients, a storage compartment 27 within the cart 20 for housing patient care supplies including at least one towel 70 for drying the patient, a back-up battery 65 in case of a power failure, and coiled extension cords 60 with electrical plugs 61 and 62 to plug into external electrical outlets to power the ice maker 30 and the water heater 40.

In use, patients in hospitals, nursing care facilities, physical therapy facilities, doctor's offices, in homes or anywhere else requiring cooled or heated liquid packs can benefit by the present invention. Encased in a compact preferably stainless steel cabinet, the rolling cart 20 that rolls up to the patient or client or other user. Inside the tanks 21 and 25 may be filled with water or other liquid. A small plastic water pump or other pump 32 and 42 can be used in each tank to pump the cooled and heated liquids to the packs. A small ice maker 30 may be used to cool the cooled water 31 and a small instant water heater 40 may be used to heat the heater water 41. Flexible tubing 33, 34, 43, and 44 may be used to take the water through the tubing up to the inflatable body cooling liquid pack 35 and heating liquid pack 45.

The input hoses 33 and 43 or tubing preferably becomes smaller as it travels closer to the packs 35 and 45. Small serpentine tubes 36 and 46 inside the packs circulate the water around in the packs. The return hoses 34 and 44 or rubber tubes allow the cooled and heated liquids 31 and 41 to drain back down from the packs into the tanks.

The cooled liquid packs 35 are generally used to reduce a fever, reduce edema in different parts of the body, and reduce pain, and swelling from post surgery clients.

The heated liquid packs 45 are generally used to increase circulation, to help in healing infections, bring relief to sore muscles, and arthritis.

Bathing and cleansing using the hose 50 and shower head 51 greatly facilitate cleaning hygiene for bedridden patients.

It is understood that the preceding description is given merely by way of illustration and not in limitation of the invention and that various modifications may be made thereto without departing from the spirit of the invention as claimed.

What is claimed is:

1. A multifunction bedside care and therapy apparatus comprising a wheeled cart comprising:
   (a) means for cooling a liquid to create a temperature controlled cooled liquid;
   (b) a tank for holding the temperature controlled cooled liquid;
   (c) a cooled liquid pack applied to a patient;
   (d) means for re-circulating the cooled liquid through the cooled liquid pack applied to the patient;
   (e) means for monitoring the temperature of the cooled liquid and for controlling the means for cooling the liquid to maintain the cooled liquid at a desired temperature;
   (f) a separate means for heating a liquid to create a temperature controlled heated liquid, a tank for holding the temperature controlled heated liquid;
   (g) a heated liquid pack applied to a patient;
   (h) means for re-circulating the heated liquid through the heated liquid pack applied to the patient;
   (i) means for monitoring the temperature of the heated liquid and for controlling the means for heating the liquid to maintain the heated liquid at a desired temperature;
   (j) a first interior space within the wheeled cart for housing the means for cooling the liquid and the tank for holding the temperature controlled cooled liquid;
   (k) a second interior space within the wheeled cart for housing the means for heating the liquid and a tank for holding the temperature controlled heated liquid;
   (l) the first and second interior spaces separated by means for thermally insulating the two interior spaces from each other;
   (m) thereby providing a multi-function bedside care and therapy system having a cooled liquid pack and heated liquid pack with cooled and heated liquid, respectively, continually circulating through them to maintain the proper temperature at all times without changing the packs; and
   (n) further comprising a hose and a shower head housed within said wheeled cart for washing patients.

2. The apparatus of claim 1 wherein the means for cooling the liquid comprises an ice maker communicating with the tank for holding the temperature controlled cooled liquid.

3. The apparatus of claim 2 wherein the means for re-circulating the cooled liquid through the cooled liquid pack comprises a cold liquid pump communicating with the tank for holding the temperature controlled cooled liquid and a cooled liquid hose transporting the temperature controlled cooled liquid from the cooled liquid pump to the cooled liquid pack on the patient and a cooled liquid hose transporting the cooled liquid from the cooled liquid pack back into the tank for holding the temperature controlled cooled liquid.

4. The apparatus of claim 1 wherein the means for heating the liquid comprises a liquid heater communicating with the tank for holding the temperature controlled heated liquid.

5. The apparatus of claim 4 wherein the means for re-circulating the heated liquid through the heated liquid pack comprises a heated liquid pump communicating with the tank for holding the temperature controlled heated liquid and a heated liquid hose transporting the temperature controlled heated liquid from the heated liquid pump to the heated liquid pack on the patient and a heated liquid hose transporting the heated liquid from the heated liquid pack back into the tank for holding the temperature controlled heated liquid.

6. The apparatus of claim 1 further comprising a storage compartment within the cart for housing patient care supplies including at least one towel for drying the patient.

7. The apparatus of claim 1 further comprising a back-up battery in case of a power failure.

8. The apparatus of claim 1 further comprising at least one coiled electrical cord connected to said wheeled cart with electrical plugs suitable for use with external electrical outlets to provide power to the means for cooling a liquid and to the means for heating a liquid.

9. The apparatus of claim 1 wherein said means for monitoring the temperature of the cooled liquid and for controlling the means for cooling the liquid to maintain the cooled liquid at a desired temperature is a thermostat that is physically associated with said cooled liquid pack applied to a patient.

10. The apparatus of claim 1 wherein said means for monitoring the temperature of the heated liquid and for controlling the means for heating the liquid to maintain the heated liquid at a desired temperature is a thermostat that is physically associated with said heated liquid pack applied to a patient.

11. A method for providing bedside care and therapy comprising:
   (a) applying a cold pack to a patient, said cold pack connected to a wheeled cart with a first set of rubber tubing and being continuously cooled by the circulation of cold water through said first set of rubber tubing and a serpentine circulating internal cooling liquid tube, said cold water being cooled by an ice machine and stored in a cold water tank contained within said wheeled cart;
   (b) applying a desired hot pack to a patient, said hot pack connected to said wheeled cart with second set rubber tubing and being continuously heated by the circulation of hot water through said second set of rubber tubing and a serpentine circulating internal heating liquid tube, said hot water being heated by a water heater and stored in a hot water tank contained within said wheeled cart;
   (c) using thermostats located on said cold pack and said hot pack to monitor the temperature of the cold water and hot water, respectively;
   (c) insulating said cold water from said hot water to prevent thermal conduction between one another;
   (d) altering the application of the cold pack and hot pack as appropriate for the patient's health; and
   (e) bathing the patient with a hose and a shower head housed within said wheeled cart for washing patients.

* * * * *